United States Patent [19]

Ishiwata et al.

[11] Patent Number: 4,782,021

[45] Date of Patent: Nov. 1, 1988

[54] METHOD OF PRODUCING L-SERINE

[75] Inventors: Kenichi Ishiwata; Nobuyoshi Makiguichi; Hideki Kawashima; Tadashi Suzuki; Masami Imadegawa, all of Kanagawa, Japan

[73] Assignee: Mitsui Toatsu Chemicals, Inc., Tokyo, Japan

[21] Appl. No.: 698,533

[22] Filed: Feb. 5, 1985

[30] Foreign Application Priority Data

Feb. 17, 1984 [JP] Japan .................................. 59-26933
Jun. 26, 1984 [JP] Japan ................................. 59-129980

[51] Int. Cl.$^4$ ........................ C12P 13/06; C12P 13/04; C12N 9/10; C12N 15/00
[52] U.S. Cl. ................................. 435/116; 435/106; 435/193; 435/849; 435/172.1
[58] Field of Search ............ 435/116, 106, 193, 172.1, 435/849

[56] References Cited

U.S. PATENT DOCUMENTS 3,755,081  8/1973  Yamade .............................. 435/116

OTHER PUBLICATIONS

Schirch, "Senne Hydroxy methyltransferase", *Advances in Enzymology*, vol. 53 (1982) John Wiley & Sons, N.Y. pp. 83–111.
Ishiwata, et al., "L-Senne Production", *Chem Absts*, vol. 103, No. 23 (Dec. 1985) p. 579 absts No. 194952a.

*Primary Examiner*—Thomas G. Wiseman
*Assistant Examiner*—Robin L. Teskin
*Attorney, Agent, or Firm*—Browdy and Neimark

[57] ABSTRACT

This invention is a method of producing L-serine by causing glycine to react with formaldehyde by using the culture solution or the microbe cells of a microorganism belonging to the genus Escherichia, having the ability of producing serine hydroxymethyltransferase and not having the practical ability of producing L-serine from glycine alone or enzymatic matter obtained through the treatment of the above culture solution or microbe cells.

In this invention, the yield of L-serine can be increased either by carrying out the reaction while maintaining aldehyde concentration at 20 mM or below or by using microbe cells of the aforementioned microorganism after they are caused to contact glycine.

4 Claims, 1 Drawing Sheet

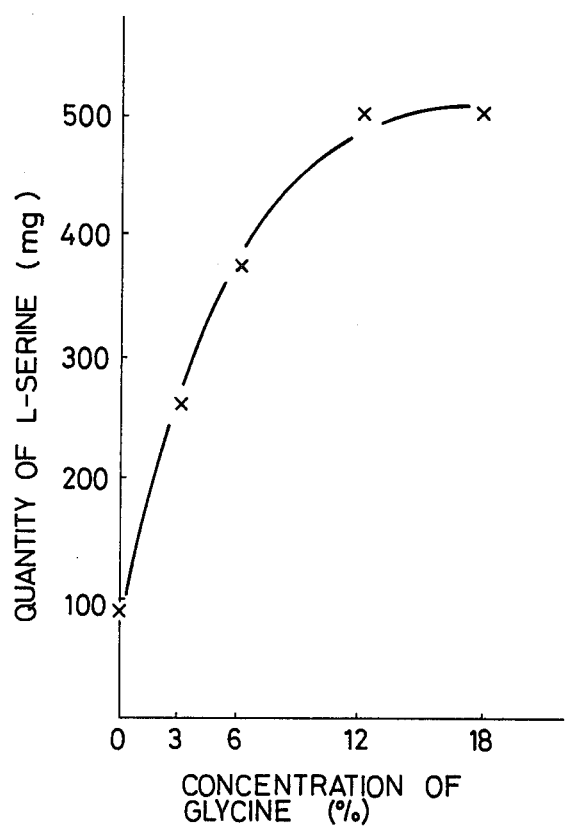

METHOD OF PRODUCING L-SERINE

BACKGROUND OF THE INVENTION

1. Field of the Invention

This invention relates to a method of producing L-serine, and more specifically, to a method of producing L-serine from glycine and formaldehyde under the existence of a microorganism having the ability of producing serine hydroxymethyltransferase.

2. Description of the Background Art

L-serine is important as an amino acid as well as drugs, cosmetics, feed additives and intermediate for drugs.

Serine hydroxymethyltransferase (E.C.2.1.2.1.) also called as either serine transhydroxymethylase or serine aldolase, widely exists in mammals, birds, higher plants, microorganisms and so forth. It is already known to catalize the reaction of synthesizing a $\beta$-hydroxyamino acid from glycine and an aldehyde carried out using pyridoxal phosphate as a coenzyme. (for example, Advances in Enzymology 53, 83–112 (1982)).

Conventionally, as a method of producing L-serine by an enzymatic method utilizing the serine hydroxymethyltransferase of a microorganism, a method of producing L-serine from either glycine alone or the combination of glycine and a minute amount of formaldehyde by using a microorganism belonging to the Proteus (Patent Publication No. 58-2677 (1983)), the Sarcina, the Flavobacterium, the Pseudomonas or the Microbacterium (Patent Laid-open No. 53-81691 (1978)) genus has been known. Every microorganism utilized in such a method has a strong activity of producing L-serine from glycine itself. Even when formaldehyde is added to prepare reaction solution, the molar ratio of L-serine produced to formaldehyde added in the reaction is only around 10 to 1. This is understood to indicate that not only serine hydroxymethyltransferase but also an enzyme catalyzing the reaction of cleaving glycine intensely participates in the reaction resulting in an extremely low yield of L-serine relative to glycine of 10% mole/mole or less. Here, since the accumulated concentration of L-serine is around 5 g/l at the most, it is hard to say that this method is a practical one.

SUMMARY OF THE INVENTION

This invention has been completed after an earnest study on the method of producing L-serine in high concentration in reaction solution in a high yield relative to glycine by utilizing serine hydroxymethyltransferase produced by a microorganism, under the existence of glycine by effectively using formaldehyde. As a result, we have found that L-serine can be produced and accumulated effectively through reaction control by using the culture solution or the microbe cells of a microorganism, belonging to the genus Escherichia and having the ability of producing serine hydroxymethyltransferase and a low or no ability of producing L-serine from glycine alone, or matter obtained through the treatment of the above solution or microbe cells.

BRIEF DESCRIPTION OF THE DRAWING

The FIGURE is a graph indicating the relationship between the concentration of glycine used for glycine treatment carried out in Example 4 and the amount of serine produced.

DETAILED DESCRIPTION OF THE INVENTION

In this invention, L-serine can be produced and accumulated in a remarkably high yield and in a notably high concentration by continuously or intermittently adding formaldehyde in such a manner as to maintain its concentration at 20 mM or below. Furthermore, in this invention, L-serine can efficiently be produced and accumulated by causing the microbe cells of the microorganism to contact glycine before glycine is caused to react with formaldehyde using the above microbe cells. Such a reaction control in this invention may be conducted alone or in a combination of two or more in order to produce and accumulate a remarkable amount of L-serine.

Especially, according to the method of this invention, a remarkably small amount of glycine remains at the end of the reaction and this markedly alleviates the burden of isolating and purifying L-serine from the reaction solution, indicating the excellence of the method of this invention as an industrial enzymatic method of producing L-serine.

A microorganism used in this invention is of the bacterial strain belonging to the genus Escherichia, having the ability of producing serine hydroxymethyltransferase and not having the practical ability of producing L-serine from glycine alone. Any bacterial strain having these properties can be used for this invention irrespective of whether it is isolated from the natural world or produced through a means such as mutation or gene recombination. For example, *Escherichia coli* MT-10350 (FERM P-7437) and *Escherichia coli* MT-10351 (FERM P-7438) can be listed.

"Not having the practical ability" said in this invention includes a case of not having as a matter of course and also includes a case of having such a weak activity as not to prevent the practice of this invention since no special hindrance is caused to the achievement of the effect of this invention in such a case.

The term "A treated enzymatic matter" indicates every matter obtained by treating the microorganism itself or its culture solution in such a manner as not to deteriorate the activity of serine hydroxymethyltransferase derived from the microorganism because this enzyme plays the main role in the practice of this invention.

In culturing a microorganism in practicing this invention, there are no special limitations to culture conditions including the medium and both of a synthetic medium and a natural medium can be used as far as they contain a source of carbon, a source of nitrogen, inorganic salts, organic nutrition and the like which can be utilized by the bacterial strain used. It is preferred that the culture be carried out under an aerobic condition at a pH of 5–9 and at a temperature of 25°–40° C.

The thus obtained culture solution itself can be used as an enzymatic source. Besides, viable microbe cells collected from the culture solution by centrifugation, filtration or the like and matter obtained by drying or treating these cells (for example, matter obtained by treating these cells through grinding, ultrasonic wave, autolysis or the like, the eluant of these cells and an enzymatic fraction obtained from the above extract) can also be used.

It is preferred that the microbe cells of the microorganism be caused to contact glycine (glycine treatment) before glycine is caused to react with an aldehyde using the above microbe cells. When the culture solution itself is used as an enzymatic source, the glycine treatment is recommended to be carried out by adding glycine to the culture solution after the culture is completed. When microbe cells collected through centrifugation, filtration or the like are used as an enzymatic source, it is recommended to suspend the collected microbe cells in a proper glycine solution. The glycine treatment, although it may be carried out either under the still condition or under the stirring condition, is desired to be carried out within the pH range of 6-9 and within the temperature range of 20°-70° C. Although a sufficient effect can be expected with 4 wt% glycine concentration, the usual glycine concentration used in this case is around 7-23%. The time of the glycine treatment, although seeming to vary according to the concentration of microbe cells, glycine concentration, temperature and so forth, is usually 30 minutes to 24 hours. Microbe cells subjected to the glycine treatment can be used as an enzymatic source for the reaction.

It is desirable that the reaction between glycine and formaldehyde according to this invention be carried out under the existence of the thus obtained glycine-treated microbe cells at a pH of 6-9 and at a temperature of 20°-60° C. under the condition of shaking or stirring.

A wide range is allowed for the concentration of glycine used as the reaction substrate. Since the usual concentration of glycine is in the range of 1-40%, glycine used as the reaction substrate may be added in its total amount at the initiation of the reaction or may be successively added in several portions with the progress of the reaction.

On the other hand, formaldehyde should be used in such a concentration as not to inhibit the enzymatic activity. It may be successively added in several portions with the progress of the reaction.

L-serine can be produced and accumulated in a high yield by maintaining formaldehyde concentration at 20 mM or below in carrying out the reaction according to this invention.

Since serine hydroxymethyltransferase requires vitamin $B^6$ as a coenzyme, the reaction is accelerated by the addition of pyridoxal phosphate to the reaction system in some cases. The reaction is accelerated by the addition of tetrahydrofolic acid used as a coenzyme to the reaction system in some cases.

This reaction is accelerated by the addition of a reducing agent or by being carried out under the condition of nitrogen feeding in some cases. In such cases, ascorbic acid, dithiothreitol, 2-mercaptoethanol, dithioerythritol, reducing glutathione, cysteine and sodium sulfite are listed as reducing agents.

In isolating L-serine produced in the reaction solution, the conventional method such as concentration or adsorption-and-desorption treatment carried out with an ion exchange resin or active carbon can be applied.

The qualitative identification of L-serine produced can be achieved through ninhydrin color development on a paper chromatogram. Its quantitative analysis can be carried out either through liquid chromatography or by cutting out a ninhydrin color development spot on the paper chromatogram before the eluant of the spot is subjected to colorimetric determination. The quantitative analysis of L-serine can be carried out by a bioassay conducted using *Leuconostoc mesenteriodes*.

In the following, the tangible description of this invention will be given according to examples and comparative examples.

EXAMPLE 1

After *Escherichia coli* MT-10350, FERM BP 793 (FERM P-7437) was grown on a bouillon slant at 37° C. for 40 hours, each of five 100-ml portions of a medium (pH 7.2) containing the nutrition indicated in Table 1 was inoculated with one platinum loop of the grown bacterium before shaking culture was performed at 37° C. for 40 hours to obtain culture solution. Next, 10 l of the medium of the above composition contained in a 20 l jar fermentor was inoculated with the above culture solution, aerated agitation culture was performed at pH 7.2 at 37° C. for 30 hours. The thus obtained culture solution was centrifuged to collect microbe cells which are then washed with physiological saline solution, thereby obtaining about 50 g of wet microbe cells. The thus obtained wet microbe cells were frozen at −15° C for two days and thawed immediately before they were used as an enzymatic source for the reaction. After 40 g of the frozen microbe cells were added to 500 ml of reaction solution containing the components indicated in Table 2, formalin was continuously supplied with a peristaltic pump in such a manner as to maintain its concentration range of 7-12 mM by analyzing the concentration of formaldehyde contained in the reaction solution through gas chromatography. The reaction was conducted at 50° C. at pH 7.0 while gently stirring the reaction solution and while feeding nitrogen gas into the reaction solution at a speed of 1 ml/min. Supply of formalin into the reaction solution was continued for 37 hours and the total amount of formalin (37% W/W formaldehyde solution) supplied into the reaction solution was 24 ml. When the reaction was completed, 29 g of L-serine was accumulated in the reaction solution. The concentration of L-serine accumulated was 55 g/l. The molar yield of L-serine produced relative to glycine added to prepare the reaction solution was 83% and that relative to formaldehyde was 86%.

TABLE 1

| Glucose | 1% | MgSO$_4$.7H$_2$O | 0.05% |
|---|---|---|---|
| Citric acid | 0.2% | Yeast extract | 0.05% |
| NaNH$_4$HPO$_4$.4H$_2$O | 0.3% | | |
| K$_2$HPO$_4$ | 0.5% | | |

TABLE 2

| Glycine | 5% |
|---|---|
| Tetrahydrofolic acid | 0.1% |
| Pyridoxal phosphate | 0.01% |

EXAMPLE 2

Reaction was conducted using *Escherichia coli* MT-10351, FERM BP 794 (FERM P-7438), different from the microorganism used in Example, by the same method as Example 1. Supply of formalin into the reaction solution was continued for 57 hours and the total amount of formalin supplied into the reaction solution was 25 ml. In the reaction solution 28 g of L-serine was accumulated. The concentration of L-serine accumulated was 53 g/l. The molar yield of L-serine produced relative to glycine added to prepare the reaction solution was 80% and that relative to formaldehyde added to the reaction solution was 80%.

The abilities of the microorganism used in this invention producing L-serine from glycine under the existence and non-existence of formaldehyde were compared. The results were as indicated in the following experimental examples.

COMPARATIVE EXAMPLE 1

100 ml of a liquid medium (pH 7.0) containing 10 g/l of meat extract, 10 g/l of peptone and 15 g/l of NaCl was inoculated with each of *Escherichia coli* MT-10350 and MT-10351, and shaking culture was performed at 30° C. for 24 hours. After the culture was completed, microbe cells were centrifuged and washed with physiological saline solution twice, thereby obtaining about 0.4 g of wet microbe cells. 0.2 g of the thus obtained wet microbe cells were suspended in 10 ml of 50 mM phosphate buffer solution (pH 7.0) containing 5,000 μmoles of glycine, 150 μmoles of formaldehyde, 10 μmoles of tetrahydrofolic acid and 0.1 μmole of pyridoxal phosphate and the mixture was subjected to reaction at 37° C. for two hours while being shaken.

As shown in Table 3, the accumulation of L-serine was observed.

Another experiment was carried out according to the same operation except that formaldehyde was not added and the following results were obtained.

TABLE 3

| Microorganism (*Escherichia coli*) | Amount of L-serine Accumulated (μmol/10 ml) | |
|---|---|---|
| | With HCHO addition | Without HCHO addition |
| MT-10350 | 140 | 12 |
| MT-10351 | 78 | 10 |

Thus, it is obvious that the microorganism used in this invention has the activity of producing L-serine from glycine and formaldehyde and does not have the practical activity of producing L-serine from glycine alone.

EXAMPLE 3

After 100 ml portions of the medium having the composition shown in Table 4 were poured into 500 ml-capacity shake flasks and sterilized, each sterilized portion was inoculated with one platinum loop of *Escherichia coli* MT-10350 grown beforehand on a bouillon slant at 37° C. for 20 hours. The shaking culture was performed at 37° C. for 15 hours. From the thus obtained culture solution, microbe cells were collected by centrifugation before being washed with physiolosical saline solution prior to being centrifuged again to obtain wet microbe cells. 1 g of the wet microbe cells were suspended in 5 ml of 18% glycine solution of pH 7.5 and gently shaken at 50° C. for three hours (glycine treatment). After the glycine solution containing the microbe cells was diluted with water to adjust the total volume to 10 ml before being adjusted to pH 7.0, 1 mg pyridoxal phosphate, 10 mg tetrahydrofolic acid and 20 mg formalin (37% formaldehyde solution) were added and reaction was initiated. The reaction was conducted at 50° C. at pH 7.0 while gently stirring the reaction solution and while feeding nitrogen gas into the reaction solution at a speed of about 1 ml/min. After the initiation of the reaction, a 10 mg portion of formalin was added to the reaction solution every 30 minutes. The reaction was continued for 20 hours and the total amount of formalin added to the reaction solution was 420 mg. In the reaction solution, 500 mg of L-serine was accumulated.

COMPARATIVE EXAMPLE 2

On the other hand, 1 g of the wet microbe cells obtained in Example 3, without being subjected to glycine treatment, were suspended in 10 ml of 9% glycine solution (pH 7.0) and the suspension was subjected to reaction by exactly the same operation as the above. As a result, only 98 mg of L-serine was accumulated in the reaction solution.

TABLE 4

| | | | |
|---|---|---|---|
| Glucose | 1% | MgSO$_4$.7H$_2$O | 0.05% |
| Citric acid | 0.2% | Yeast extract | 0.05% |
| NaNH$_4$HPO$_4$.4H$_2$O | 0.3% | | |
| K$_2$HPO$_4$ | 0.5% | | |

EXAMPLE 4 AND COMPARATIVE EXAMPLE 3

Wet microbe cells of *Escherichia coli* MT-10350 were obtained by the same method as that used in Example 3. After 1 g of the wet microbe cells were suspended in 5 ml of each of glycine solutions (adjusted to pH 7.5) with concentrations shown in Table 5, the suspension was gently shaken at 50° C. for three hours. Next, water and glycine were added to the glycine solution containing microbe cells so as to adjust glycine concentration to 9% and the total amount to 10 ml. Following that, this was subjected to reaction by the same method as Example 1. During the reaction, a total amount of 420 mg of formalin was added to each reaction solution. The quantities of L-serine produced in the reaction solutions were as indicated in Table 5.

TABLE 5

| Glycine Concentration for Glycine Treatment (%) | Quantity of L-Serine Produced (mg) |
|---|---|
| 0 | 90 |
| 3 | 261 |
| 6 | 375 |
| 12 | 498 |
| 18 | 497 |

EXAMPLE 5 AND COMPARATIVE EXAMPLE 4

The same operation as that used in Example 3 was performed using *Escherichia coli* MT-10351. As a result, in the reaction solution prepared by using glycine-treated microbe cells, 370 mg of L-serine was accumulated. In the reaction solution prepared by using microbe cells which had not undergone any glycine treatment, the amount of L-serine accumulated was as small as 39 mg.

EXPERIMENTAL EXAMPLE 1

Determination of Serine Hydroxymethyltransferase Activity

Wet microbe cells obtained according to the method described in Example 3 of Example 5 were suspended in 50 mM potassium phosphate buffer solution (containing 0.5 mM of pyridoxal phosphate) of pH 7.0, and the suspension was subjected to ultrasonic treatment at 4° C. for five minutes. After the thus obtained treated solution was centrifuged (10,000 g, five minutes), the serine hydroxymethyltransferase activity existing in the supernatant was measured according to the method of R. T. Taylor et al. (Analytical Biochemistry, 13, 80–84 (1965)).

The measurements of specific activity determined are indicated in Table 6.

TABLE 6

| Bacterial Strain | Specific Activity [μ-mole-HCHO/ minute/mg protein] |
|---|---|
| *Escherichia coli* MT-10350 (FERM P-7437) | 340 |
| *Escherichia coli* MT-10351 (FERM P-7438) | 230 |

What is claimed is:

1. A method of producing L-serine by reacting glycine with formaldehyde in the presence of serine hydroxymethyltransferase, which comprises the step of: culturing, in a first culture medium containing glycine, tetrahydrofolic acid and formaldehyde, said formaldehyde being present at a concentration of no more than 20 mM, a microorganism belonging to the genus Escherichia and selected from the group consisting of *Escherichia coli* MT-10350, FERM BP-793 (FERM P-7437) or *Escherichia coli* MT-10351, FERM BP-794 (FERM P-7438), said microorganism having the ability to produce serine hydroxymethyltransferase and essentially lacking the ability to produce L-serine from glycine in the absence of formaldehyde, while maintaining the formaldehyde concentration in said culture medium at 20 mM or below.

2. A method of producing L-serine according to claim 1, further comprising the step of culturing the microorganism in a second culture medium containing glycine but not formaldehyde before culturing said microbe cells in said first culture medium.

3. A method of producing L-serine, which comprises causing glycine to react with formaldehyde in the presence of serine hydroxymethyltransferase available by using the culture solution or the microbe cells of at least one member selected from the group consisting of *Escherichia coli* MT-10350, FERM P-7437 (FERM BP-793) and *Escherichia coli* MT-10351, FERM P-7438 (FERM BP-794) having the ability of producing serine hydroxymethyltransferase and not having the ability of producing L-serine from glycine alone, the reaction being carried out while aldehyde concentration being maintained at 20 mM or below.

4. A method of producing L-serine according to claim 1, wherein the culture solution or the microbe cells are caused to contact glycine and then subjected to the reaction.

* * * * *